United States Patent
Yokoyama et al.

(10) Patent No.: US 8,724,110 B2
(45) Date of Patent: May 13, 2014

(54) PROCESS FOR PREDICTING TINT STRENGTH OF COATING COMPOSITIONS BY WET COLOR MEASUREMENT

(71) Applicant: E I du Pont de Nemours and Company, Wilmington, DE (US)

(72) Inventors: Ayumu Yokoyama, Wallingford, PA (US); Rajesh Gopalan Saliya, Philadelphia, PA (US); Anthony Moy, Garnet Valley, PA (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 0 days.

(21) Appl. No.: 13/666,526

(22) Filed: Nov. 1, 2012

(65) Prior Publication Data

US 2013/0141724 A1 Jun. 6, 2013

Related U.S. Application Data

(60) Provisional application No. 61/554,222, filed on Nov. 1, 2011.

(51) Int. Cl.
*G01J 3/46* (2006.01)
*G01N 1/00* (2006.01)

(52) U.S. Cl.
USPC .............................. 356/402; 356/36

(58) Field of Classification Search
USPC .......................... 356/402, 36, 445
See application file for complete search history.

(56) References Cited

U.S. PATENT DOCUMENTS

| 4,204,766 | A | * | 5/1980 | Harada .......................... 356/404 |
| 4,236,486 | A | * | 12/1980 | Nakamine et al. ............... 399/59 |
| 4,936,685 | A | * | 6/1990 | Taylor et al. ................... 356/409 |
| 5,249,029 | A | * | 9/1993 | Sommer et al. ................ 356/336 |
| 6,091,914 | A | * | 7/2000 | Yoo .................................. 399/57 |
| 6,292,264 | B1 | * | 9/2001 | Voye et al. ..................... 356/445 |
| 6,583,878 | B2 | * | 6/2003 | Hustert ........................... 356/402 |
| 2012/0189764 | A1 | * | 7/2012 | Yokoyama et al. ................ 427/8 |
| 2012/0191416 | A1 | * | 7/2012 | Yokoyama et al. ........... 702/189 |
| 2013/0107266 | A1 | * | 5/2013 | Moy et al. ...................... 356/445 |
| 2013/0141713 | A1 | * | 6/2013 | Saliya et al. .................... 356/36 |
| 2013/0141727 | A1 | * | 6/2013 | Yokoyama et al. ............ 356/445 |

FOREIGN PATENT DOCUMENTS

DE 2525701 A1 * 12/1976 ................ G01J 3/46

* cited by examiner

*Primary Examiner* — Tarifur Chowdhury
*Assistant Examiner* — Violeta Prieto
(74) *Attorney, Agent, or Firm* — Ingrassia Fisher & Lorenz, P.C.

(57) ABSTRACT

The present invention is directed to a process for predicting the tint strength of a pigmented coating composition, such as automotive OEM or refinish paint, on a real time basis while it is being made. The tint strength of a coating resulting from a layer, obtained by adding a reference binder to the coating composition, is measured. The process is repeated by subjecting the coating compositions to successive grinding intervals. The tint strength vs. reflectance is plotted on a graph and then by using a curve fitting equation, a tint strength prediction curve is obtained. By measuring the reflectance of a wet layer of a target coating composition, the tint strength of that target coating composition can then be predicted by using the tint strength prediction curve. The process is most useful during the manufacture of coating compositions, such as automotive OEM and refinishes paints.

17 Claims, 3 Drawing Sheets

PROCESS FOR PREDICTING TINT STRENGTH OF COATING COMPOSITIONS BY WET COLOR MEASUREMENT

CROSS-REFERENCE TO RELATED APPLICATION

This application claims priority under 35 U.S.C. §119 from U.S. Provisional Application Ser. No. 61/554,222, filed Nov. 1, 2011, which is hereby incorporated by referenced in its entirety.

FIELD OF INVENTION

The present invention is directed to a process of predicting the tint strength of a pigmented coating composition. The process is more particularly directed to a quality assurance process that predicts on a real time basis, the tint strength of automotive OEM and refinish paints while such paints are being manufactured.

BACKGROUND OF INVENTION

A tint is generally any hue (color) that has been mixed with white. Tint strength is a measure of how strongly a particular color or pigment affects (or tints) another one when mixed with it. Some pigments (for instance phthalo blue) have a very strong tinting ability, meaning a small quantity will have a great effect on another color or pigment when mixed with it. Others (for instance burnt sienna) have a weak tinting ability, meaning a small quantity will have minimal impact on another color when mixed with it. The tinting ability of paint is generally affected by the size of the pigment particle and how well the pigment particles have been dispersed within paint. The tinting ability of paint is generally improved by grinding a pigment mixture added to the other conventional components of paint, such as binders, solvents and type of conventional grinding devices, such as ball mills used and the duration of grinding. Determining the fineness of paint's grind is important, because a grind, which is too coarse may reduce the paint's color uniformity, gloss, and opacity. The longer the grinding time, the finer would be the pigment particle size. However, if the grinding time is too long, it may not be economically a viable and moreover it could adversely affect the size, i.e., reduce the flake size of some of the paint components, such as metallic flakes generally added to produce a metallic paint to an unacceptable level. Obviously if the grinding time is too short, it would have adverse effect on the tint strength of paint.

Thus, knowing the tint strength of a coating composition while it is being made is very important to a paint maker for producing coating composition of known and uniform tint qualities. Therefore, a paint manufacturer typically would check a sample of a coating composition, such as automotive OEM paint or refinish paint, while it is being made to determine its tint strength. One way to check the tint strength is to use Hegman grind gage, which allows a paint maker to determine how finely ground the particles of pigment (or other solid) are dispersed in a sample of a coating composition by using the procedure described in ASTM D1210. The gage consists of a steel block with a series of very small parallel grooves machined into it. The grooves decrease in depth from one end of the block to the other, according to a scale stamped next to them. A typical Hegman gage is 170 mm by 65 mm by 15 mm, with a channel of grooves running lengthwise, 12.5 mm across and narrowing uniformly in depth from 100 μm to zero. A puddle of a sample of a coating composition is placed at the deep end of the gage and then drawing the coating composition down with a flat edge along the grooves. The paint fills the grooves, and the location where a regular, significant "pepperyness" in the visual appearance of the coating appears, marks the coarsest-ground dispersed particles. The reading is then taken from the scale marked next to the grooves, in dimensionless units called "Hegman units" and/or in mils or micrometers. So from time to time, an aliquot of such coating compositions being manufactured is taken and its tint strength is visually observed with tint measuring devices, such as Hegman grind gage. The process parameters are then adjusted and the aforedescribed testing procedure is repeated until the adjusted coating composition falls within desired tint strength.

However, the aforementioned testing procedure is not only time consuming and cumbersome but it is also not very sensitive to changes to tint strength during the grinding process since the aforementioned procedure involves visual observation, which can change from one observer to the next. As a result, even though the Hegman grind gage may indicate an acceptable level of grinds, the batch-to-batch quality of the resulting coating compositions can be still detrimentally affected due it insensitivity to grinding intervals. Therefore, a need exists to develop a process that could more accurately predict the tint strength of a coating composition while it is still being manufactured such that the manufacturing process could be readily adjusted on a real time basis to get the desired tint strength.

STATEMENT OF INVENTION

The present invention is directed to a tint strength prediction process comprising:

(a) dispensing on a test substrate a $L_0$ layer of a substantially uniform thickness of an aliquot of a $S_0$ coating composition containing pigments through a vessel of a tint strength prediction device containing said $S_0$ coating composition;

(b) projecting on said $L_0$ layer a beam of light of a preset intensity at a preset angle of incidence from a light source;

(c) measuring $B_0$ reflectance of said beam reflected from said $L_0$ layer at a preset angle of reflectance by an optical measurement instrument;

(d) measuring $Y_0$ tint strength of a $M_0$ coating composition comprising a reference binder and said $S_0$ coating composition;

(e) grinding $S_0$ coating composition for $T_1$ grinding interval to produce $S_1$ coating composition;

(f) repeating steps (a) through (d) to determine $B_1$ reflectance of a $L_1$ layer of said $S_1$ coating composition and $Y_1$ tint strength of a $M_1$ coating composition comprising said reference binder and said $S_1$ coating composition;

(g) iteratively grinding $S_1$ coating composition for $T_2$ to $T_n$ grinding intervals to produce $S_2$ to $S_n$ coating compositions;

(h) repeating said steps (a) through (d) for $S_2$ to $S_n$ coating compositions to determine $B_2$ to $B_n$ reflectances of $L_2$ to $L_n$ layers and $Y_2$ to $Y_n$ tint strengths of $M_2$ to $M_n$ coating compositions wherein n ranges from 4 to 20, wherein $M_2$ to $M_n$ coating compositions, respectively comprise said reference binder and said $S_2$ to $S_n$ coating compositions;

(i) storing said $B_0$ to $B_n$ reflectances of said $L_0$ to $L_n$ layers and said $Y_0$ to $Y_n$ tint strengths of $M_1$ to $M_n$ coating compositions in a non-transitory computer usable storage medium of a computer;

(j) locating intersecting points on a graph where said $B_0$ to $B_n$ of said $L_0$ to $L_n$ layers on X-axis of said graph intersect with said $Y_0$ to $Y_n$ tint strength of said $M_1$ to $M_n$ coating compositions on Y-axis of said graph;

(k) using a curve fitting equation to produce a tint strength prediction curve on said graph;

(l) dispensing on said test substrate a $L_T$ layer of said substantially uniform thickness of an aliquot of a target coating composition through said vessel of said tint strength prediction device, said target tint dispersion having been ground for $T_T$ grinding interval;

(m) projecting on said $L_T$ layer a beam of light at said preset intensity and at said preset angle of incidence from said light source;

(n) measuring $B_T$ reflectance of said beam reflected from said $L_T$ layer at said preset angle of reflectance by said optical measurement instrument;

(o) locating said $B_T$ of said $L_T$ layer on said X-axis of said graph;

(p) locating an intersecting point on said tint strength prediction curve that intersects with said $B_T$ on said X-axis of said graph; and (q) predicting $Y_T$ tint strength of said target coating composition by locating said $Y_T$ tint strength on said Y-axis of said graph that intersects with said intersecting point on said tint strength prediction curve that intersects with said $L_T$ on said X-axis of said graph.

The step (d) in the aforedescribed process comprises:

(a1) dispensing on a tint strength substrate a $R_{REF}$ layer of said substantially uniform thickness produced from said reference binder;

(b1) curing or drying said $R_{REF}$ layer into a $C_{REF}$ coating;

(c1) projecting on said $C_{REF}$ coating said beam of light of said first preset intensity at said preset angle of incidence from said light source;

(d1) measuring $D_{REF}$ reflectance of said $C_{REF}$ coating by said an optical measurement instrument;

(e1) dispensing on a tint strength substrate a $R_0$ layer of said substantially uniform thickness produced from said $M_0$ coating composition;

(f1) curing or drying said $R_0$ layer into a $C_0$ coating;

(g1) projecting on said $C_0$ coating said beam of light of said first preset intensity at said preset angle of incidence from said light source;

(h1) measuring $D_0$ reflectance of said $C_0$ coating by said optical measurement instrument; and (h2) computing said $Y_0$ tint strength of said $M_0$ coating composition by using the formula:

$$[(D_{REF}-D_0)/D_{REF}]\times 100.$$

DETAILED DESCRIPTION OF PREFERRED THE EMBODIMENT

As defined herein:

"Coating composition" means a coating composition that contains binders, solvents, inorganic pigments, organic pigments, aluminum flakes, mica flakes, inorganic flakes, organic flakes, flatting agent, dispersing agents or a combination thereof that imparts color to a coating from a coating composition when applied over a substrate, such as an automotive body, bumper or a fender.

While producing a coating composition, various components of a coating composition, such as pigments, flakes, binders, solvents, etc, are mixed and are typically ground in grinding mills, such as ball mills. Therefore, ascertaining the tint strength of a coating composition while it is being made is highly desirable as the grind time can be adjusted to attain desired tint strength.

Applicants have unexpectedly discovered that a gloss of a layer from a coating composition in its wet state when measured can directly correlate to the tint strength of that coating composition. The process and the device of the present invention provide a solution to attain the aforedescribed correlation.

Figure 1:
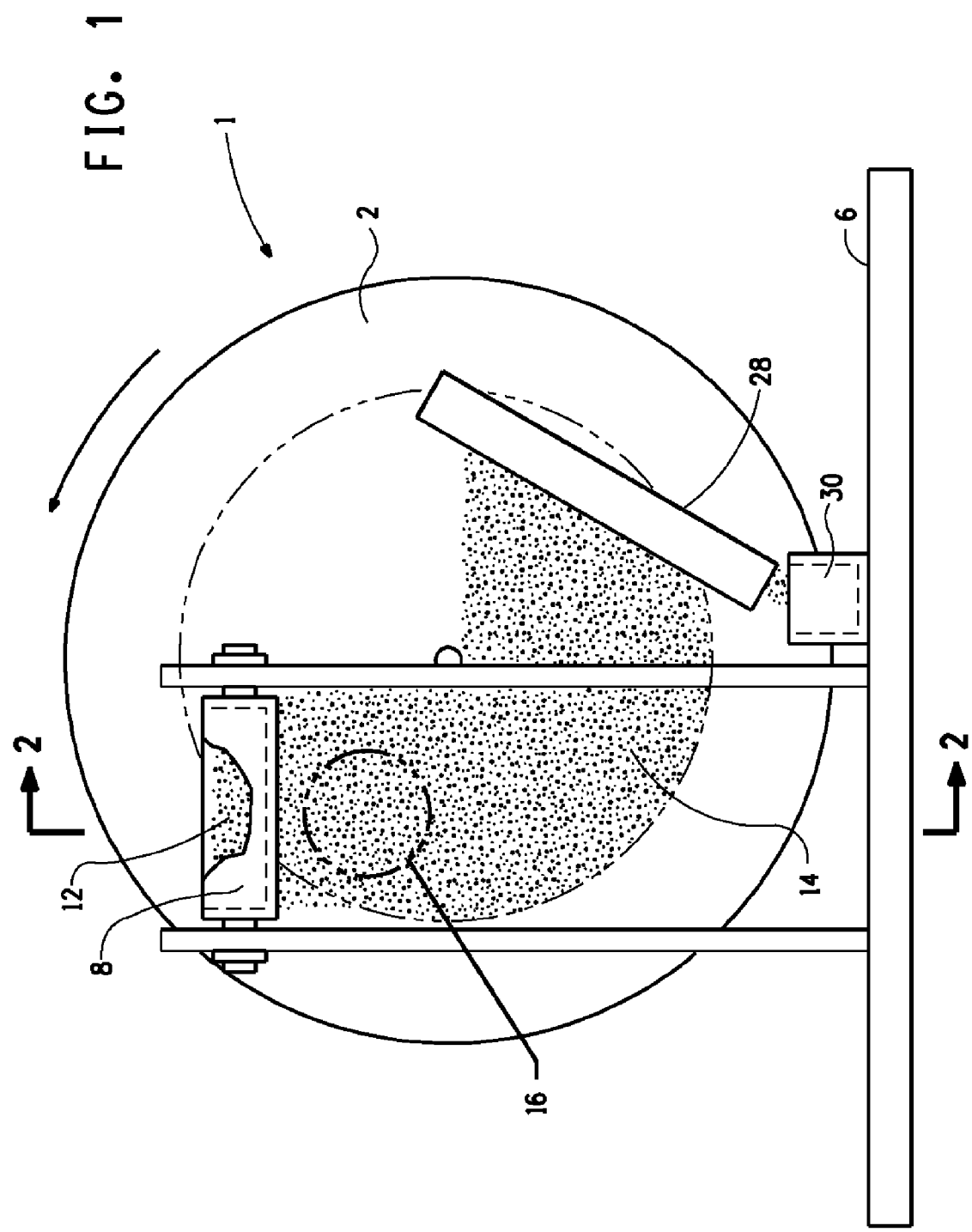
FIGS. 1 and 2 broadly illustrate one of the embodiments of a flake amount prediction device of the present invention.
Figure 2:
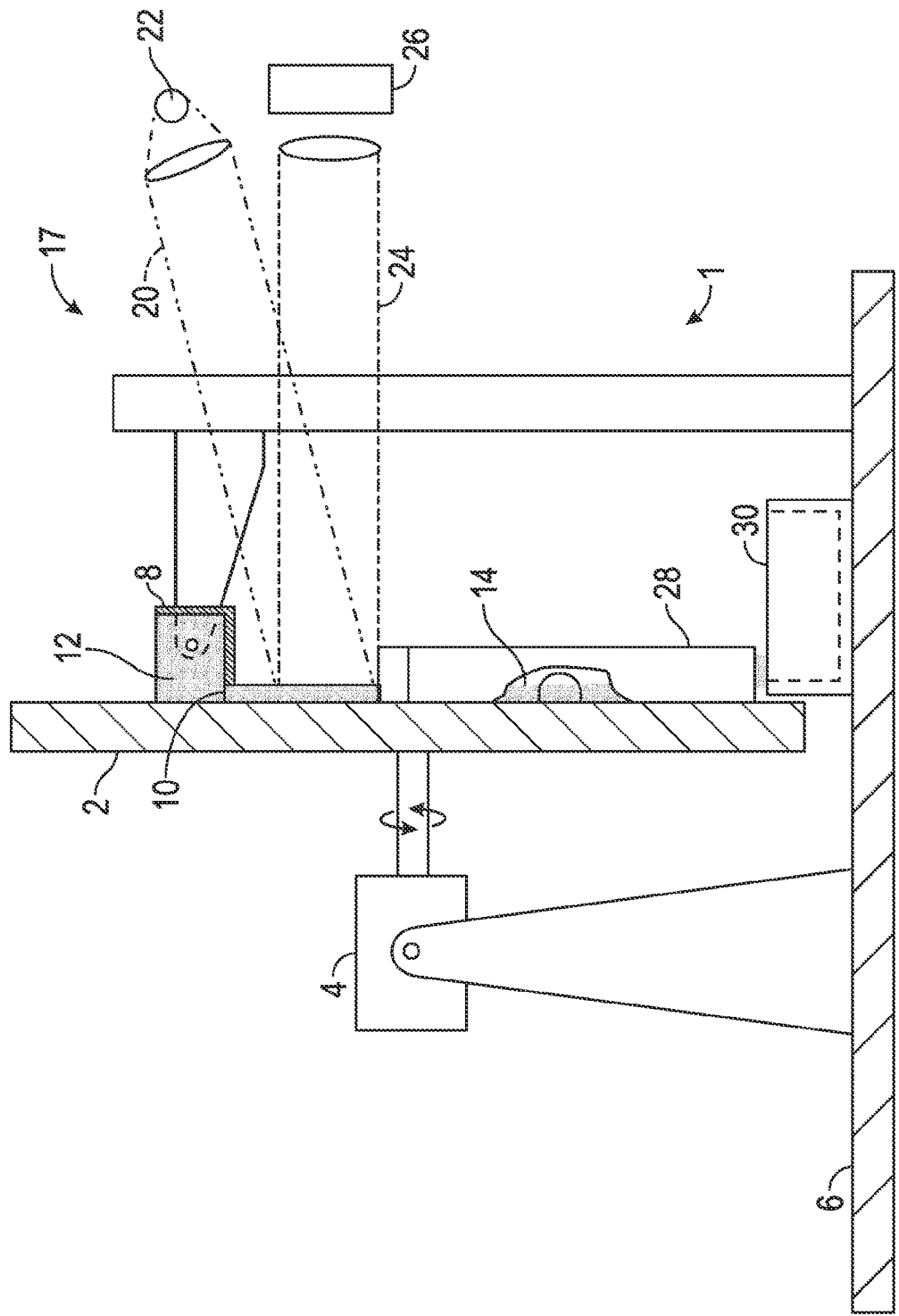

One of the tint strength prediction devices suitable for the process of the present invention includes a device 1 shown in FIGS. 1 and 2. Device 1 includes a test substrate 2, preferably a disc, rotated by a driver 4, such as an electric motor, which is positioned on a support frame 6. Test substrate 2 mounted on a shaft of driver 4 can be positioned either in a horizontal or in a vertical position. Test substrate 2 of device 2 shown in FIGS. 1 and 2 is positioned vertically, which is preferred. Test substrate 2 can be made of any suitable material, such as steel, plastic or aluminum. The surface of test substrate 2 preferably has the same degree of smoothness as that of, for example, auto body or auto bumper such that the results obtained are as close to those that would have been obtained under the similar paint application conditions.

As shown in FIG. 1, Device 1 is provided with a vessel 8 positioned adjacent to test substrate 2. Vessel 8 is provided with an opening 10, preferably a slot, through which a $S_0$ coating composition 12, when poured into vessel 8, can be applied as a $L_0$ layer 14 of a substantially uniform thickness on a measurement area 16 on the surface of test substrate 2. $S_0$ coating composition 12 includes conventional components such as binders, solvents, inorganic pigments, organic pigments, aluminum flakes, mica flakes, inorganic flakes, organic flakes, flatting agent, dispersing agents or a combination thereof. As test substrate 2 is rotated by driver 4, preferably for about a quarter turn, $L_0$ layer 14 is created. Opening 10 is adjacent to substrate 2 such that a resulting gap between opening 10 and substrate 2 controls the thickness of $L_0$ layer. Typically, $L_0$ layer is provided with a thickness that can range from 6 micrometers to 2300 micrometers.

Tint strength prediction device 1 of the present invention includes a conventional optical mechanism 17 provided with conventional collimators for producing a beam of light 20 of preset intensity at a preset angle that can be projected on measurement area 16 from a conventional light source 22. A conventional optical measurement instrument 26 typically measures conventional L,a,b color data on the reflectance of a surface color wherein L factor or value refers to lightness or darkness, "a" factor or value refers to (+a) redness to greenness (−a) and "b" factor or value refers to (+b) yellowness to blueness (−b). The applicants have unexpectedly discovered that the use of data from "a" value reported as ("B reflectance" above) results in the closest curve fitting of the data. Any angle of incidence and reflectance can be used. However, a 45 degree angle of reflectance is typically employed and is preferably measured before there is substantial change in the optical characteristics of $L_0$ layer 14 that depend on the physical and chemical properties of the coating composition from which $L_0$ layer 14 is produced. Thus, the higher the content of the solvent in the coating composition, the longer would be the window during which the reflectance can be measured and vice versa. Coating compositions that are lacquers (those containing high molecular weight non-reactive binder polymers dissolved in a solvent) typically would have longer measurement window than coating compositions that are enamels (those containing binder polymers containing reactive groups that chemically react with crosslinking groups on crosslinking agents that are mixed before being applied as a layer on a substrate). Generally, $B_0$ reflectance 24 is measured within 2 seconds to two minutes after $L_0$ layer 14 is applied over test substrate 2. A $B_0$ reflectance 24 of beam of light 20 off of $L_0$ layer 14 can then be measured by optical measurement instrument 26, such as MA-68 gloss measurement device supplied by X-Rite of Grand rapids, Mich.

Before, after or along with the measurement of $B_0$ reflectance, a $R_{REF}$ layer made from a conventional reference binder, such as LS-9615 white binder supplied by DuPont Company of Wilmington, Del., having substantially the same thickness as $L_0$ layer 14 is applied over a tint reference substrate, such as substrate 2, is conventionally applied or applied by means of device 1 under the steps disclosed above. $R_{REF}$ layer is dried or cured into a $C_{REF}$ coating.

A beam of light, such as beam of light 20 of the first preset intensity at the first preset angle of incidence from a light source, such as light source 22 is projected on $C_{REF}$ coating. $D_{REF}$ reflectance 24, off of $C_{REF}$ coating is then measured by conventional optical measurement instrument, such as optical measurement instrument 26 (MA-68 gloss measurement device supplied by X-Rite of Grand rapids, Mich.), (not-shown in FIG. 1) at the preset angle, which is preferably 45 degrees. If desired a duplicate layer of same thickens as $L_0$ layer can be applied on another similar substrate including a glass substrate by suitable means such as doctor blade. After drying and/or curing into a duplicate coating same as $C_0$ coating whose $D_0$ reflectance can then be measured. The applicants have unexpectedly discovered that the use of data from "L" value reported as ("D reflectance" above) results in the closest curve fitting of the data.

An aliquot of $S_0$ coating composition is added to the aforedescribed reference binder to produce $M_0$ coating composition. The aforedescribed process is then repeated to obtain $D_0$ reflectance of $C_0$ coating produced from $M_0$ coating composition.

$Y_0$ tint strength of $M_0$ coating is computed by using the following formula;

$$[(D_{REF}-D_0)/D_{REF}]\times 100.$$

Means for configuring computer readable program code devices is used to cause a conventional computer to store $B_0$ reflectance 24 of $L_0$ layer 14 and $Y_0$ tint strength of $M_0$ coating composition in a computer usable storage medium of the computer (not-shown in FIG. 1). The computer is preferably in communication with optical measurement instrument 26. If desired, the computer can be in communication with a remote computer, such as an offsite computer used to gather information from one or more computers connected to tint strength prediction devices of the present invention.

If desired, after $Y_0$ tint strength of $C_0$ coating is measured, substrate 2 can be rotated further by driver 4 to scrape off $C_0$ coating with a doctor blade 28 into a waste container 30 and substrate 2 can then be cleaned. Alternatively, after $Y_0$ tint strength of $C_0$ coating is measured, substrate 2 can be removed and $C_0$ coating scraped off substrate 2 and then cleaned.

Thereafter, $S_0$ coating composition is ground using conventional grinders, such as ball mills, for a $T_1$ grinding interval to produce $S_1$ coating composition. By utilizing the aforedescribed steps, $S_1$ coating composition is dispensed over the tint substrate or over substrate 2 to produce layer $L_1$ whose $B_1$ reflectance is then measured. Thereafter, an aliquot of $S_1$ composition is added to the reference binder to obtain $M_1$ coating composition, which is then applied over the tint substrate or over substrate 2 and then dried and/or cured to produce $C_1$ coating. Its $D_1$ reflectance is then measured by the aforedescribed steps and $Y_1$ tint strength of $S_1$ coating composition is then computed by using the formula:

$$[(D_{REF}-D_1)/D_{REF}]\times 100.$$

Thereafter, $S_1$ coating composition is iteratively ground for $T_2$ to $T_n$ grinding intervals to successively produce $S_2$, $S_3$, $S_4$, $S_5$ ... to $S_n$ coating compositions, wherein n ranges from 4 to 20. By iterative, it is meant that $S_1$ is ground for $T_2$ grinding interval to produce $S_2$ coating composition, which is then further ground for $T_3$ grinding interval to produce $S_3$ coating composition, which is then further ground for $T_4$ grinding interval to produce $S_4$ grinding interval, and so on. An aliquot of each iteratively produced $S_2$ to $S_n$ coatings compositions is applied as $L_2$ to $L_n$ layers over substrate 2 of device 1 to measure $B_2$ to $B_n$ reflectances by the process described above. Simultaneously, an aliquot of each iteratively produced $S_2$ to $S_n$ coatings compositions is mixed with the reference binder to produce $M_2$ to $M_n$ coating compositions applied as $C_2$ to $C_n$ coatings whose $D_2$ to $D_n$ reflectances were then measured by the process described above. Applicants have unexpectedly discovered that L-value from $D_1$ to $D_n$ reflectances is most suited for the process of the current invention. As noted earlier $Y_1$ to $Y_n$ tint strength is computed by using the formula:

$$[(D_{REF}-D_n)/D_{REF}]\times 100.$$

The aforementioned $M_1, M_2, \ldots M_n$ coating compositions, preferably utilized the same ratio of $S_0, S_1, \ldots S_n$ coating compositions to the reference binder. Preferably, the amount of $S_0, S_1, \ldots S_n$ coating compositions are mixed with the reference binder ranges from 1 weight percent to 20 weight percent based on the total weight of $M_1, M_2, \ldots M_n$ coating compositions, respectively. As described above, $B_1$ reflectance 24 from a $L_1$ layer 14 from $S_1$ coating composition and $Y_1$ tint strength of $C_1$ coating obtained from $M_1$ coating composition is measured and the means for configuring computer readable program code devices is used to cause the computer to store $B_1$ reflectance 24 of $L_1$ layer 14 and $Y_1$ tint strength of $C_1$ coating in the computer usable storage medium of the computer. The process is repeated until $B_n$ reflectance from a $L_n$ layer 14 and $Y_n$ tint strength of $C_n$ coating from $M_n$ coating composition is measured and stored in the computer usable storage medium of the computer. The aforementioned $T_1$ to $T_n$ grinding intervals can range from ¼ hour to 100 hours.

The means for configuring computer readable program code devices is used to cause the computer to locate intersecting points on a graph where $B_0$ to $B_n$ reflectances of $L_0$ to $L_n$ layers 14 on X-axis of the graph intersect with the $Y_0$ to $Y_n$ tint strengths in percentage of $C_0$ to $C_n$ coatings, respectively based on $M_0$ to $M_n$ coating compositions, on Y-axis of the graph. The means for configuring computer readable program code devices is then used to cause the computer to use a curve fitting equation to produce a tint strength prediction curve on the graph. Preferably, the curve fitting equation is a second degree polynomial equation. More preferred second degree polynomial equation is of the following formula:

$$\text{Tint strength } Y=a(B_n)^2+b \tag{1}$$

$$R^2=Z \tag{2}$$

wherein said constants a, b and $R^2$ are determined by a curve fitting process, such as that described in Microsoft Office Excel® 2003 supplied by Microsoft Corporation of Redmond, Wash. Z is a statistical measure of how close the curve fits to the experimental datum points on a graph. When Z is equal to 1, it is considered to be an ideal fit, i.e., all the experimental datum points lay on the fitted curve. All the necessary and relevant information is stored on the computer usable storage medium.

If desired, the tint strength prediction curve on the graph may be displayed on a conventional monitor and/or printed on paper by means of a conventional printer both of which being in communication with the computer. Once the tint strength prediction curve on the graph is produced, the user can use the tint strength prediction device of the present invention to control the tint strength of a target coating composition without going through the cumbersome and time consuming process of curing the layer into a coating and then measuring its tint strength by tint strength measuring devices, such as Hegman grind gage, which is not sensitive to changes occurring to a coating composition during the grinding process. $L_T$ layer 14 (also know as target layer) from the target coating composition, preferably having the same substantially uniform thickness as the layers used in creating the tint strength prediction curve, is dispensed over substrate 2 of tint strength prediction device 1 of the present invention in a production set up that allows the manufacturer of a coating composition to expeditiously adjust the ingredients of the coating composition for ensuring that the resulting coating composition has a desired tint strength.

As described above, $B_T$ reflectance 24 from $L_T$ layer 14 from the target coating composition is measured and the means for configuring computer readable program code devices is used to cause the computer to store $B_T$ reflectance 24 of $L_T$ layer 14 in the computer usable storage medium of the computer.

The means for configuring computer readable program code devices is used to cause the computer to locate $B_T$ reflectance of $L_T$ layer on the X-axis of the graph. The means for configuring computer readable program code devices is used to cause the computer to locate an intersecting point on the tint strength prediction curve that intersects with $B_T$ on X-axis of the graph. Finally, The means for configuring computer readable program code devices is used to cause the computer to predict the tint strength of a target coating resulting from $L_T$ layer by locating $Y_T$ tint strength on the Y-axis of the graph that intersects with the intersecting point on the flake amount prediction curve that intersects with $B_T$ on the X-axis of the graph.

As a result, once the tint strength prediction curve is stored in a computer of device 1, an aliquot of a coating composition being made can be applied as a layer and its wet gloss measured to predict the tint strength of a coating resulting from said composition. If the tint strength falls outside of the desired specification, the manufacturing process can be adjusted in real time without interruption by monitoring and adjusting the grinding time on a continuing basis.

Few of the aspects of the aforedescribed tint strength prediction device 1 of the present invention are described in German patent application DT 25 25 701 A1. It should be understood that substrate 2 need not be positioned vertically or have to have a disc shape. Other embodiments, such as those where substrate is positioned horizontally, or is in the form of a belt, etc. are also well suited for the process of the present invention. For example, substrate in the form of a roller, as described in a commonly assigned U.S. Pat. No. 6,583,878 to Hustert, is also well suited for the process of the present invention.

EXAMPLES

A blue dispersion was prepared by using the following ingredients:

TABLE 1

| Ingredients | Weight in grams |
| --- | --- |
| t-butyl acetate solvent | 83.7 |
| Disperbyk 183 dispersent[1] | 26.2 |
| Joncryl 924 acrylic polyol[2] | 211.6 |
| Total | 321.5 |

[1]supplied by BYK Chemie of Marietta, Georgia
[2]supplied by BASF of Iselin, New Jersey.

A mixture containing 0.02 grams of the aforedescribed blue dispersion ($S_0$ coating composition) and 20 grams of Joncryl 924 was acrylic polyol was prepared, which was then applied over substrate 2 of device 1 and its reflectance $B_0$ was measured by using the process described above before said $S_0$ coating composition was subjected to grinding step. A coating of LS-9615 reference binder supplied by DuPont Company of Wilmington, Del. was applied as a coating ($C_{REF}$ coating) and its $B_{REF}$ reflectance was obtained by using the process described above. A mixture of 0.2 grams of the blue dispersion ($S_0$ coating composition) and 25 gram of LS-9615 reference binder was made ($M_0$ coating composition), which was then applied as a coating ($C_0$ coating) and it $D_0$ reflectance was obtained by using the process described above. $Y_0$ tint strength, which is a percentage compared to a reference binder was then computed by using the formula:

$$[(D_{REF}-D_0)/D_{REF}] \times 100.$$

$S_0$ coating composition was then iteratively ground for grinding intervals shown in Table 2 below and aliquots of the sequential coating compositions as they were iteratively ground were measured for their reflectances and tint strengths. By way of comparison, the tint strength in the form of the fineness of ground pigment particles dispersed in coating compositions were also measured by using Hegman grind gage by means of a process provided in ASTM D2012:

TABLE 2

| Compositions | Grinding time in hours | B Reflectances (a-value) of L layers | Y Tint Strength as % of reflectances (L-value) of C coatings | Comparative Hegman fineness |
| --- | --- | --- | --- | --- |
| $S_0$ | 0 | 5.9 ($B_0$) | 61.2 ($Y_0$ of $C_0$) | 7.5 |
| $S_1$ | 5 | 4.98 ($B_1$) | 63.3 ($Y_1$ of $C_1$) | 7.75 |
| $S_2$ | 7 | 4.15 ($B_2$) | 66.6 ($Y_2$ of $C_2$) | 7.75 |
| $S_3$ | 9 | 4.03 ($B_3$) | 67.5 ($Y_3$ of $C_3$) | 7.75 |
| $S_4$ | 12 | 3.15 ($B_4$) | 70.7 ($Y_4$ of $C_4$) | 7.75 |

Figure 3:
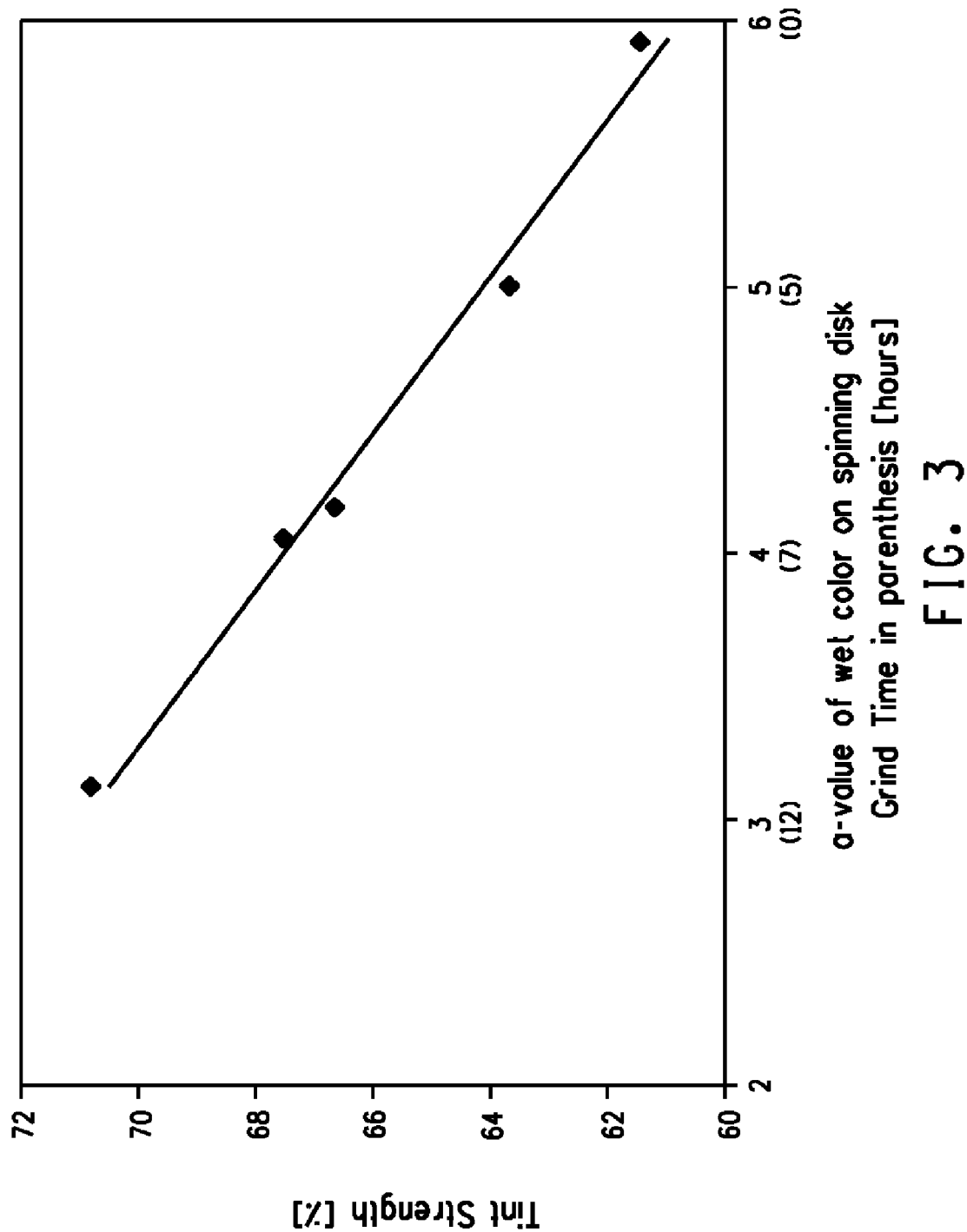
FIG. 3 broadly illustrates the tint strength prediction curve produced by the tint strength prediction process of the present invention.

The foregoing data points were plotted by using the process provided above. As shown in FIG. 3, intersecting points on a graph where $B_0$ to $B_n$ of $L_0$ to $L_n$ layers on X-axis of the graph intersect with $Y_0$ to $Y_n$ tint strengths of $S_0$ to $S_n$ coating compositions on Y-axis of the graph are then located.

Using a curve fitting equation, such as the aforementioned secondary degree polynomial equation (1) is then used to produce a tint strength prediction curve, such as that shown in FIG. 3. The term "a" in the equation (1) was −3.5034. The term "b" in the equation (1) was 81.429. The statistical measure Z was 0.9841. All of the foregoing terms were obtained by using the aforementioned Microsoft Excel® program. It would be readily to apparent to one of ordinary skill in the art that the statistical measure Z of 0.9841 indicates the curve of the tint strength prediction was a very close fit to the Z of the ideal fit of 1. By way of comparison, one can readily notice that the conventional Hegman grind gage was quite insensitive to the tint strength changes occurring to the coating composition as it was ground iteratively.

The process of the present invention is then used to predict the tint strength of a target coating composition by first dispensing on substrate 2 a $L_T$ layer of preferably the same substantially uniform thickness of a target coating composition through vessel 8 of tint strength prediction device 1 containing the target coating composition after a known hours of grinding whose tint strength is unknown. A beam of light 20 at the preset intensity and at the preset angle of incidence from light source 22 is then projected on measurement area 16 of $L_T$ layer and a value of $B_T$ reflectance of beam reflected from $L_T$ layer at the preset angle of reflectance (45 degrees) is measured by optical measurement instrument 26. An intersecting point on the tint strength prediction curve that intersects with $B_T$ reflectance on the X-axis of said graph is then located and tint strength at the preset gloss angle of a coating after a known grinding interval resulting from $L_T$ layer is then predicted by locating $Y_T$ on the Y-axis of the graph.

Thus, one of ordinary skill in the art can readily see that the tint strength of a coating can be readily predicted by the tint strength prediction curve of the process of the present invention by just measuring the reflectance of a wet layer of a coating composition after known hours of grinding.

The process and device of the present invention is most suitable for ensuring that the tint strength of automotive OEM and refinish paints resulting from coatings therefrom falls within a desired range.

What is claimed is:

1. A tint strength prediction process comprising:
   (a) dispensing on a test substrate a $L_0$ layer of a substantially uniform thickness of an aliquot of a $S_0$ coating composition containing pigments through a vessel of a tint strength prediction device containing said $S_0$ coating composition;
   (b) projecting on said $L_0$ layer a beam of light of a preset intensity at a preset angle of incidence from a light source;
   (c) measuring $B_0$ reflectance of said beam reflected from said $L_0$ layer at a preset angle of reflectance by an optical measurement instrument;
   (d) measuring $Y_0$ tint strength of a $M_0$ coating composition comprising a reference binder and said $S_0$ coating composition;
   (e) grinding $S_0$ coating composition for $T_1$ grinding interval to produce $S_1$ coating composition;
   (f) repeating steps (a) through (d) to determine $B_1$ reflectance of a $L_1$ layer of said $S_1$ coating composition and $Y_1$ tint strength of a $M_1$ coating composition comprising said reference binder and said $S_1$ coating composition;
   (g) iteratively grinding $S_1$ coating composition for $T_2$ to $T_n$ grinding intervals to produce $S_2$ to $S_n$ coating compositions;
   (h) repeating said steps (a) through (d) for $S_2$ to $S_n$ coating compositions to determine $B_2$ to $B_n$ reflectances of $L_2$ to $L_n$ layers and $Y_2$ to $Y_n$ tint strengths of $M_2$ to $M_n$ coating compositions wherein n ranges from 4 to 20, wherein $M_2$ to $M_n$ coating compositions, respectively comprise said reference binder and said $S_2$ to $S_n$ coating compositions;
   (i) storing said $B_0$ to $B_n$ reflectances of said $L_0$ to $L_n$ layers and said $Y_0$ to $Y_n$ tint strengths of $M_1$ to $M_n$ coating compositions in a non-transitory computer usable storage medium of a computer;
   (j) locating intersecting points on a graph where said $B_0$ to $B_n$ of said $L_0$ to $L_n$ layers on X-axis of said graph intersect with said $Y_0$ to $Y_n$ tint strength of said tint strength of said $M_1$ to $M_n$ coating compositions on Y-axis of said graph;
   (k) using a curve fitting equation to produce a tint strength prediction curve on said graph;
   (l) dispensing on said test substrate a $L_T$ layer of said substantially uniform thickness of an aliquot of a target coating composition through said vessel of said tint strength prediction device, said target tint dispersion having been ground for $T_T$ grinding interval;
   (m) projecting on said $L_T$ layer a beam of light at said preset intensity and at said preset angle of incidence from said light source;
   (n) measuring $B_T$ reflectance of said beam reflected from said $L_T$ layer at said preset angle of reflectance by said optical measurement instrument;
   (o) locating said $B_T$ of said $L_T$ layer on said X-axis of said graph;
   (p) locating an intersecting point on said tint strength prediction curve that intersects with said $B_T$ on said X-axis of said graph; and
   (q) predicting $Y_T$ tint strength of said target coating composition by locating said $Y_T$ tint strength on said Y-axis of said graph that intersects with said intersecting point on said tint strength prediction curve that intersects with said $L_T$ on said X-axis of said graph.

2. The process of claim 1 wherein said step (d) comprises:
   (a1) dispensing on a tint strength substrate a $R_{REF}$ layer of said substantially uniform thickness produced from said reference binder;
   (b1) curing or drying said $R_{REF}$ layer into a $C_{REF}$ coating;
   (c1) projecting on said $C_{REF}$ coating said beam of light of said preset intensity at said preset angle of incidence from said light source;
   (d1) measuring $D_{REF}$ reflectance of said $C_{REF}$ coating by said an optical measurement instrument;
   (e1) dispensing on a tint strength substrate a $R_0$ layer of said substantially uniform thickness produced from said $M_0$ coating composition;
   (f1) curing or drying said $R_0$ layer into a $C_0$ coating;
   (g1) projecting on said $C_0$ coating said beam of light of said preset intensity at said preset angle of incidence from said light source;
   (h1) measuring $D_0$ reflectance of said $C_0$ coating by said an optical measurement instrument; and
   (h2) computing said $Y_0$ tint strength of said $M_0$ coating composition by using the formula:

$$[(D_{REF}-D_0)/D_{REF}] \times 100.$$

3. The process of claim 1 wherein said $T_1$ to $T_n$ are successive grinding intervals.

4. The process of claim 1 wherein said $T_1$ to $T_n$ are of the same duration.

5. The process of claim 1 wherein said optical measurement instrument is a spectrophotometer.

6. The process of claim 1 wherein said optical measurement instrument is in communication with said computer.

7. The process of claim 1 wherein said tint strength prediction device is in communication with said computer.

8. The process of claim 1 wherein the thickness of said $L_0$ to $L_n$ layers is controlled by an opening adjacent to said test substrate through which said $S_0$ to $S_n$ coating compositions flow.

9. The process of claim 1 wherein said $L_0$ to $L_n$ layers are of the same thickness ranging from 6 micrometers to 2300 micrometers.

10. The process of claim 1 wherein said test substrate is a disc positioned substantially vertically on a support frame of said tint strength prediction device.

11. The process of claim 1 wherein said curve fitting equation is a second degree polynomial equation.

12. The process of claim 11 wherein said second degree polynomial equation is of the formula:

Tint strength $Y=a(B_n)^2+b$ $R^2=Z$ wherein said constants a, b and Z are determined by a curve fitting process.

13. The process of claim 1 comprising displaying said predicted tint strength of said target coating on a CRT monitor.

14. The process of claim 1 comprising communicating said predicted tint strength of said target coating from said computer to a remote computer.

15. The process of claim 1 wherein said $T_1$ to $T_n$ grinding intervals range from ¼ hour to 100 hours.

16. The process of claim 1 wherein said coating composition is an automotive OEM or refinish paint.

17. The process of claim 16 wherein said coating composition comprises inorganic pigments, organic pigments, aluminum flakes, mica flakes, inorganic flakes, organic flakes, flatting agent, dispersing agents or a combination thereof.

* * * * *